United States Patent [19]

Hara et al.

[11] Patent Number: 4,913,909

[45] Date of Patent: Apr. 3, 1990

[54] COMPLEX OF TEA-LEAF EXTRACT AND ACTIVE ALUMINUM HYDROXIDE

[75] Inventors: Yukihiko Hara, Shizuoka; Hajime Asai, Nagoya; Tadashi Kitamikado, Inuyama; Hajimu Yamamoto, Nagoya; Kazuo Okushio, Shizuoka; Kozo Nakamura, Tokyo, all of Japan

[73] Assignee: Mitsui Norin Co., Ltd., Tokyo, Japan

[21] Appl. No.: 914,716

[22] Filed: Oct. 2, 1986

[51] Int. Cl.$^4$ ............... A61K 31/35; A61K 33/08
[52] U.S. Cl. ................... 424/688; 424/195.1; 549/399; 514/456
[58] Field of Search ............ 549/399; 424/195.1, 424/157, 688; 514/456

[56] References Cited

U.S. PATENT DOCUMENTS

| 2,472,476 | 6/1949 | Hardt | 424/157 |
| 3,975,202 | 8/1976 | Emblem et al. | 501/127 |
| 4,003,999 | 1/1977 | Lybrand et al. | 424/195.1 |
| 4,005,191 | 1/1977 | Clark | 424/157 |
| 4,248,789 | 2/1981 | Okada | 549/399 |
| 4,613,672 | 9/1986 | Hara | 549/399 |
| 4,673,530 | 6/1987 | Hara | 549/399 |

OTHER PUBLICATIONS

"Anti-inflammatory Activity of (−)-Epicatechin, A Bioflavonoid Isolated from *Anacardium occidentale* Linn" by T. Swarenalakshmi et al, Indian J. Pharm. Sci. 1981, 43, pp. 205–208.

Journal of Pharmaceutical Sciences, vol. 65, No. 8 (Aug. 1976, pp. 1188–1191).

Horita et al. *Chem Abs*, 89, 12190n (1978).

*Primary Examiner*—John W. Rollins
*Assistant Examiner*—W. Catchpole
*Attorney, Agent, or Firm*—Frishauf, Holtz, Goodman & Woodward

[57] ABSTRACT

Extract of tea leaves or (−)-epigallocatechin gallate as the principal ingredient of the extract forms a complex with active aluminum hydroxide. The animal test using rats has established that these complexes have therapeutic effect for gastric ulcers, e.g. pylorus-ligated ulcer and indomethacin-induced ulcer, when orally administered. Tests were also undertaken for the effect on the secretion of gastric juice and acute toxicity of these complexes using rats and mice as the test animals.

3 Claims, No Drawings

COMPLEX OF TEA-LEAF EXTRACT AND ACTIVE ALUMINUM HYDROXIDE

BACKGROUND OF THE INVENTION

The present invention relates to a complex of tea-leaf extract, of which the principal ingredient is (—)-epigallocatechin gallate, referred to as EGCg hereinbelow, and active aluminum hydroxide or a complex of the EGCg per se and active aluminum hydroxide.

The complex of the present invention has excellent antiulcer activity, antipeptic activity and antacid activity so that it is useful as a therapeutic medicine for digestive ulcers. The complex of the present invention is a novel material not known in the prior art.

The inventors have previously undertaken extensive investigations on an industrial method for the preparation of tealeaf extract containing EGCg as the principal ingredient, which is one of the starting materials for the preparation of the inventive complex, and the results are disclosed in Japanese Patent Kokai No. 59-219384 (See also U.S. Pat. No. 4,673,530). They further have continued investigations on a method for the fractionation of catechin compounds from the tea-leaf extract and the results are disclosed in Japanese Patent Kokai No. 60-13780 (See also U.S. Pat. No. 4,613,672).

Applications directed to tea-leaf extracts which have been filed so far, describes either astringent and antioxidation activities or the catechin compounds present in the extract. However, there are no reports concerning antiulcer or antipeptic activity for tea-leaf extracts.

Ulcers have a diversity of origins and there have developed a diversity of medications to deal with them. Furthermore, it is usual to administer two or more medicaments depending on the therapeutic requirements. Among the known medicaments are anticholinergic agents, $H_2$-receptor antagonists and antipeptic agents. Sulcralfate is the known antipeptic agent, but it is not as effective as desired.

SUMMARY OF THE INVENTION

An object of the present invention is therefore to provide a novel therapeutic medicament for digestive ulcers having higher antipeptic activity than the prior art medicaments accompanied by high safety in administration.

Another object of the invention is to provide a therapeutic medicament for digestive ulcers based on the previously developed tea-leaf extract.

Thus, the present invention provides a complex of tea-leaf extract, of which the principal ingredient is (—)-epigallocatechin gallate, and active aluminum hydroxide and a complex of the (—)-epigallocatechin gallate per se and active aluminum hydroxide. These complexes exhibit strong antiulcer, antipeptic and antacid activities with greatly decreased toxicity and no astringency inherent in the tea-leaf extract.

DETAILED DESCRIPTION OF THE PREFERRED EMBODIMENTS

The above described invention has been completed on the basis of an unexpected discovery that a complex is formed between tea-leaf extract or fractionation product thereof and active aluminum hydroxide and that the complex is insoluble in water without astringency and with greatly decreased toxicity exhibiting some therapeutic activity. Namely, tealeaf extract, of which the principal ingredient is EGCg, or EGCg per se as a fractionation product of tea-leaf extract can be reacted with active aluminum hydroxide to form a complex having high activity as a therapeutic medicament of digestive ulcers with the least toxicity in oral administration.

The complex of the invention can be prepared in the following manner. The first step is the preparation of the tea-leaf extract according to the procedure described in, for example, Japanese Patent Kokai No. 59-219384 by extracting tea leaves with hot water or a hydrophilic organic solvent, washing the extract solution with chloroform to transfer the extracted matter into the organic phase and distillation of the organic solvent to leave the extracted material in a dry form.

Further, the tea-leaf extract obtained in the above described manner is fractionated by high-performance liquid chromatography using a reverse phase column according to the procedure described in Japanese Patent Kokai No. 60-13780 (See also U.S. Pat. No. 4,613,672) to give EGCg as the fractionation product. The tea-leaf extract, of which the principal ingredient is EGCg, or the fractionated EGCg is dissolved in a solvent which is a hydrophilic organic solvent or, preferably, water to prepare a solution for the reaction with active aluminum hydroxide.

The term active aluminum hydroxide is used to denote the gel-like aqueous suspension which is obtained by adding an aqueous alkali solution to an aqueous solution of, for example, aluminum chloride or aluminum hydroxychloride. The alkaline compound used as the above mentioned aqueous alkaki solution is exemplified by sodium hydroxide, sodium carbonate, sodium bicarbonate, potassium hydroxide, potassium carbonate and the like. Typically and preferably, the aqueous alkali solution is a 1N aqueous solution of sodium hydroxide.

The gel-like aqueous suspension of active aluminum hydroxide is then admixed with the aqueous solution of the tea-leaf extract or EGCg and the mixture is vigorously agitated for 10 to 30 minutes at a temperature of 5° to 30° C. followed by standing overnight to give the desired complex of the invention.

The following examples illustrate the procedure for the preparation of the inventive complexes in more detail and the results of the animal tests. Illustrated are therapeutic activity of the complexes against several types of gastric ulcers in rats acute toxicity testing.

EXAMPLE 1

A complex of tea-leaf extract and active aluminum hydroxide was prepared in the following manner. 3 g of a tea-leaf extract containing 60% of EGCg, 15% of (—)-epicatechin gallate, referred to as ECg hereinbelow, 15% of (—)-epigallocatechin, referred to as EGC hereinbelow, and 7% of (—)-epicatechin, referred to as EC hereinbelow, were dissolved in 30 ml of water to prepare an aqueous solution. 4.2 g of aluminum hydroxychloride $Al_2(OH)_5Cl$ were dissolved in 36 ml of water and 24 ml of a 1N aqueous solution of sodium hydroxide were added thereto under vigorous agitation to give a highly viscous, milky-white suspension.

The thus prepared aqueous suspension of active aluminum hydroxide was then admixed with 30 ml of the aqueous solution of the tea-leaf extract containing the catechin compounds with vigorous agitation followed by standing overnight. The supernatant was discarded and the precipitate was collected by filtration, washed with water and dried to give 3.8 g of a brown solid containing 18.4% of aluminum which was a complex of the tea-leaf extract and active aluminum hydroxide.

EXAMPLE 2

A complex of EGCg and active aluminum hydroxide was prepared in the following manner. Thus, an aqueous solution of 3.6 g of aluminum hydroxychloride in 33 ml of water was admixed with 47 ml of a 1N aqueous solution of sodium hydroxide under vigorous agitation to give a highly viscous, milky-white suspension. This aqueous suspension of active aluminum hydroxide was admixed with an aqueous solution of 10 g of EGCg in 50 ml of water under vigorous agitation followed by standing overnight. The supernatant was discarded and the precipitate was collected by filtration, washed with water and dried to give 9.1 g of a brown solid containing 16.5% of aluminum which was a complex of EGCg and active aluminum hydroxide.

EXAMPLE 3

The complexes prepared in Examples 1 and 2, referred to as ATM and AEGCg, respectively, hereinbelow, were tested for the therapeutic activity against gastric ulcers of rats such as pylorus-ligated or indomethacin-induced ulcers.

Thus, according to the method of Shay, et al. described in Gastroentorology, volume 5, page 43 (1945), a group of ten male rats of Wistar strain each having a body weight of about 200 g were used as the test animals. After fasting 48 hours each rat was put to etherization and the stomach was ligated at the pyloric part. Immediately after the ligation, the rat was orally administered with a suspension of the ATM or AEGCg in a 5% solution of gum arabic. The control group was fed only the solution of gum arabic without either ATM or AEGCg. After 18 hours of abstinence from food and water, the rat was killed and the stomach was excised and incised along the greater curvature to examine the condition of ulcer appearing on the forestomach. Table 1 below summarizes the results obtained with the animals belonging to the control group, test groups administered with different doses of AEGCg or ATM and comparative group administered with sucralfate.

TABLE 1

|  | Dose (mg/kg, p.o.) | Ulcer index | Suppression (%) |
|---|---|---|---|
| Control | — | 4.89 ± 0.11 | — |
| AEGCg | 10 | 4.33 ± 0.33 | 11.5 |
| AEGCg | 30 | 2.13 ± 0.74** | 56.4 |
| AEGCg | 100 | 0*** | 100 |
| ATM | 100 | 2.50 ± 0.62** | 48.9 |
| Sucralfate | 100 | 2.86 ± 0.40** | 41.5 |

**P < 0.01
***P < 0.001

Separately, according to the method of Somogi, et al. disclosed in J. Pharm. Pharmac., volume 21, page 122 (1969), a group of light male rats of Wistar strain each having a body weight of about 200 g were used to test the therapeutic effect of the complexes against indomethacin ulcers. Each of the rats belonging to the test group was, after 24 hours of fasting, orally administered with ATM or AEGCg suspended in a 5% solution of gum arabic followed by oral administration of indomethacin in a dose of 25 mg/kg body weight after 30 minutes from the administration of the ATM or AEGCg. After 7 hours abstinence from food and water, the rat was killed and the stomach was excised and incised along the greater curvature to measure the length of the ulcers appearing on the glandular stomach. The overall length of the ulcers is given in Table 2 below as the ulcer index. The control group was treated in the same manner as above excepting ATM or AEGCg in the gum arabic solution.

TABLE 2

|  | Dose (mg/kg, p.o.) | Ulcer index (mm) | Suppression (%) |
|---|---|---|---|
| Control | — | 35.4 ± 4.7 | — |
| AEGCg | 25 | 27.0 ± 4.0 | 23.7 |
| AEGCg | 50 | 15.0 ± 3.4** | 57.6 |
| AEGCg | 100 | 10.1 ± 1.5*** | 71.5 |
| ATM | 100 | 12.6 ± 1.9*** | 64.4 |
| Cimetidine | 100 | 13.3 ± 2.8*** | 62.4 |

**P < 0.01
***P < 0.001

Further, the complexes were subjected to the test for the antipeptic activity or the effect on the secretion of gastric juice in rats according to the method of Shay, et al. Thus, a group of eight male rats of Wistar strain each having a body weight of about 200 g were used as the test animals. After 24 hours of fasting, the stomach of each rat was ligated at the pyloric part under etherization. Immediately after the ligation, the rat was orally administered with ATM or AEGCg suspended in a 5% solution of gum arabic. After 6 hours of abstinence from food and water, the rat was again etherized to take out the stomach as ligated at the cardiac end. The gastric juice in the stomach was put to centrifugal separation to give a supernatant of which the volume, overall acidity and overall peptic activity were measured to give the results shown in Table 3.

TABLE 3

|  | Dose (mg/kg, p.o.) | Volume of gastric juice (ml/rat) | Overall acidity (mEq/liter) | Peptic activity (mg tyrosine) | Suppression (%) |
|---|---|---|---|---|---|
| Control | — | 6.92 ± 0.52 | 90.9 ± 3.9 | 900.5 ± 87.1 | — |
| AEGCg | 30 | 6.98 ± 0.45 | 97.1 ± 3.9 | 599.5 ± 66.2* | 33.4 |
| AEGCg | 100 | 8.03 ± 0.57 | 90.1 ± 3.8 | 506.0 ± 39.1** | 43.8 |
| AEGCg | 300 | 7.48 ± 0.53 | 90.8 ± 5.2 | 73.9 ± 58.1*** | 91.8 |
| ATM | 100 | 6.98 ± 0.62 | 82.5 ± 3.9 | 584.6 ± 75.4* | 35.1 |
| Sucralfate | 200 | 7.98 ± 0.39 | 85.4 ± 3.8 | 585.3 ± 68.0* | 35.0 |

*p < 0.05
**p < 0.01
***p < 0.001

Lastly, ATM and AEGCg were subjected to the test of acute toxicity by male mice of ddY strain each having a body weight of 20 to 25 g. After fasting overnight, the mice were orally administered with ATM or AEGCg with varied doses to determine the 50% lethal dose ($LD_{50}$). The results were that the $LD_{50}$ value of each of the ATM and AEGCg was more than 10 g/kg while the values of the starting tea-leaf extract and the EGCg were 2.17 g/kg and 2.5 g/kg, respectively.

What is claimed is:

1. A complex of a tea-leaf extract containing (—)-epigallocatechin gallate as the principal ingredient and active aluminum hydroxide.

2. A complex consisting essentially of (—)-epigallocatechin gallate and active aluminum hydroxide.

3. A method for suppressing gastic ulcers in mammals comprising orally administering to the mammal in need of such treatment an effective amount of the complex of claim 1.

* * * * *